(12) United States Patent
Zajc et al.

(10) Patent No.: US 12,279,859 B2
(45) Date of Patent: *Apr. 22, 2025

(54) METHOD FOR OPERATING AN ORTHOPEDIC DEVICE AND CORRESPONDING DEVICE

(71) Applicants: Otto Bock Healthcare Products GmbH, Vienna (AT); ASKLEPIOS KLINIK ALSBACH GMBH, Alsbach-Haehnlein (DE)

(72) Inventors: Johannes Zajc, Vienna (AT); Andreas Augsten, Frankfurt (DE)

(73) Assignees: OTTO BOCK HEALTHCARE PRODUCTS GMBH, Vienna (AT); ASKLEPIOS KLINIK ALSBACH GMBH, Alsbach-Haehnlein (DE)

( * ) Notice: Subject to any disclaimer, the term of this patent is extended or adjusted under 35 U.S.C. 154(b) by 417 days.

This patent is subject to a terminal disclaimer.

(21) Appl. No.: 17/616,600
(22) PCT Filed: Jun. 5, 2020
(86) PCT No.: PCT/EP2020/065687
§ 371 (c)(1),
(2) Date: Dec. 3, 2021
(87) PCT Pub. No.: WO2020/245398
PCT Pub. Date: Dec. 10, 2020

(65) Prior Publication Data
US 2022/0233854 A1    Jul. 28, 2022

(30) Foreign Application Priority Data
Jun. 5, 2019 (DE) ..................... 10 2019 115 096.5

(51) Int. Cl.
*A61B 5/11* (2006.01)
*A61F 2/64* (2006.01)
(Continued)

(52) U.S. Cl.
CPC ............... *A61B 5/112* (2013.01); *A61F 2/64* (2013.01); *A61F 2/70* (2013.01); *A61F 5/0102* (2013.01);
(Continued)

(58) Field of Classification Search
CPC ........................... A61B 5/112; A61N 1/36031
(Continued)

(56) References Cited

U.S. PATENT DOCUMENTS

| 5,831,937 A | 11/1998 | Weir et al. |
| 2007/0050044 A1 | 3/2007 | Haynes et al. |

(Continued)

FOREIGN PATENT DOCUMENTS

| CN | 104394806 A | 3/2015 |
| CN | 106821680 A | 6/2017 |

(Continued)

OTHER PUBLICATIONS

International Search Report and Written Opinion issued in PCT/EP2020/065687, mailed Dec. 10, 2020, 3 pgs.
(Continued)

*Primary Examiner* — Nadia A Mahmood
(74) *Attorney, Agent, or Firm* — HOLLAND & HART LLP

(57) ABSTRACT

The invention relates to a method for operating an orthopedic device, which supports a first body part of a wearer and has at least one controllable actuator, wherein the method includes a) determining a chronological progression of at least one parameter, which allows a conclusion to be drawn regarding a state of motion of the wearer, from measurement values of at least one sensor, b) detecting the state of motion from the at least one determined chronological progression and c) controlling the at least one controllable actuator depending on the detected state of motion, wherein, for detecting the state of motion, at least the chronological progression of at least one parameter of a second body part of the wearer is also used.

11 Claims, 3 Drawing Sheets

(51) Int. Cl.
  *A61F 2/70* (2006.01)
  *A61F 5/01* (2006.01)
  *A61N 1/36* (2006.01)
  *A61F 2/60* (2006.01)
  *A61F 2/68* (2006.01)

(52) U.S. Cl.
  CPC ..... *A61N 1/36003* (2013.01); *A61N 1/36031* (2017.08); *A61B 2505/09* (2013.01); *A61F 2002/607* (2013.01); *A61F 2002/608* (2013.01); *A61F 2002/6818* (2013.01); *A61F 2002/6827* (2013.01); *A61F 2002/701* (2013.01)

(58) Field of Classification Search
  USPC .......................................................... 607/49
  See application file for complete search history.

(56) References Cited

U.S. PATENT DOCUMENTS

| | | |
|---|---|---|
| 2009/0043357 A1 | 2/2009 | Tong et al. |
| 2011/0216075 A1 | 9/2011 | Shigeta et al. |
| 2013/0237884 A1 | 9/2013 | Kazerooni et al. |
| 2014/0012164 A1 | 1/2014 | Tanaka |
| 2015/0190248 A1 | 7/2015 | Vitello et al. |
| 2017/0119550 A1 | 5/2017 | Sankai |
| 2018/0042654 A1 | 2/2018 | Ingvarsson et al. |
| 2018/0147074 A1 | 5/2018 | Battlogg |
| 2018/0311054 A1 | 11/2018 | Schroeder |

FOREIGN PATENT DOCUMENTS

| | | |
|---|---|---|
| CN | 109562265 A | 4/2019 |
| DE | 4119150 A1 | 12/1992 |
| DE | 10 2014 117 663 A1 | 12/2014 |
| DE | 10 2016 114 075 B3 | 11/2017 |
| EP | 2616115 A1 | 7/2013 |
| EP | 2863846 A1 | 4/2015 |
| EP | 3156010 A1 | 4/2017 |
| JP | 2012-135486 A | 7/2012 |
| JP | 2014-027978 A | 2/2014 |
| JP | 2014-042605 A | 3/2014 |
| JP | 6168488 B2 | 6/2017 |
| JP | 2017-205213 A | 11/2017 |
| WO | 2012/037555 A1 | 3/2012 |
| WO | 2013/190495 A1 | 12/2013 |

OTHER PUBLICATIONS

Meyns Pieter et al., "The how and why of arm swing during human walking," Gait & Posture, Elsevier, Amsterdam, NL, vol. 38, No. 4, Mar. 13, 2013, pp. 555-562.

China Patent Office "Office Action", issued in connection with China Patent Application No. 202080039870.3 dated May 23, 2024.

International Search Report and Written Opinion issued in PCT/EP2020/065690, Dec. 10, 2020.

METHOD FOR OPERATING AN ORTHOPEDIC DEVICE AND CORRESPONDING DEVICE

CROSS-REFERENCE TO RELATED APPLICATIONS

This is a national phase application of International Application No. PCT/EP2020/065687, filed 5 Jun. 2020, which claims the benefit of German Patent Application No. 10 2019 115 096.5, filed 5 Jun. 2019, the disclosures of which are incorporated herein, in their entireties, by this reference.

TECHNICAL FIELD

The invention relates to a method for operating an orthopedic device that supports or replaces a first body part of a wearer and comprises at least one controllable actuator, wherein the method features the following steps:
a) determining a chronological profile of at least one parameter, which allows for a conclusion to be drawn about a movement status of the wearer, from measurement values of at least one sensor,
b) detecting the movement status from the at least one determined chronological profile, and
c) controlling the at least one controllable actuator depending on the detected movement status.

BACKGROUND

In particular, orthopedic devices are particularly orthoses that are produced for limbs, i.e. arms and/or legs, of a wearer. An orthopedic device is usually arranged on a single limb, i.e. a single leg or a single arm, of the wearer.

An orthosis supports the respective body part. On the one hand, this comprises the support and protection against excessive strain, for example in a post-operative healing process by limiting an angular range in which a joint is to be used, for example, by means of an orthosis. Support within the scope of the present invention also includes support by relieving strain, which is achieved, for example, in sports orthoses or also in so-called exoskeletons, i.e. portable mechanical structures equipped with actuators if required, which are used in the medical field, for example, in rehabilitation or as an alternative to wheelchairs. There does not necessarily have to be a limitation of the user. For example, the use of such an orthosis/exoskeleton is also possible to reduce the strain on the body during physical activities, to increase performance and/or to reduce the risk of injury.

It is important and of considerable advantage to know the movement status of the wearer in order to adapt the controllable actuator accordingly. Detectable movement statuses include, for instance, climbing and descending stairs, walking on a ramp, walking and running at different speeds, standing, sitting, climbing over obstacles that are in one's way, or a movement characteristic of a routine task. All of these different movement statuses often require different controls of the controllable actuator.

It is important to differentiate between a movement status of the wearer of an orthopedic device described above and the movement status or the movement of the respective body part. For example, when walking on level ground, the movement status of the wearer of the orthopedic device does not change as long as walking on level ground continues. However, the movement of the body part, for example a knee, changes multiple times during each step. It goes through standing phases and swing phases with different key moments, such as the heel strike. The detection and prediction of these key moments is also important for the control of an orthopedic device and has been known from the prior art for many years. In the scope of the invention described here, however, the detection of the movement status of the wearer of the orthopedic device is the primary focus as well as the question of how a change in movement status can be detected and the control of the orthopedic device adapted accordingly.

Consequently, the movement status of a wearer usually lasts for several step cycles, while the movement status of a body part changes on a much shorter time scale. This change can happen multiple times within a single step cycle. The at least one controllable actuator is preferably provided and configured to change the movement status of a body part, namely the first body part that is supported or replaced by the orthopedic device. In principle, it is not configured to change the movement status of the wearer of the orthopedic device.

With a controllable actuator, it may be, for example, a damping element, such as a hydraulic damper. In the case of hydraulic dampers, valves in particular are present in a fluid connection which can preferably be opened or closed in an infinite manner. The cross-section of the fluid connection is thus increased or decreased, by which the resistance against a flow of fluid and thus the damping caused by the damping element can be reduced or increased.

The controllable actuator may be a final control element by way of which a certain movement of at least one part of the orthopedic device or the entire orthopedic device can be controlled. For example, in the case of active orthopedic devices, such as active knee joints or active ankle joints, this is necessary so that the joint of the orthopedic device performs the desired function. Controllable actuators can be designed to be active or passive, regardless of whether they are damping elements or final control elements.

In particular, means and methods for stimulating the musculoskeletal system, especially electro-stimulation of muscles and nerves, for example by means of electrodes, are also considered to be controllable actuators within the meaning of the present invention. These can be arranged, for example, on the wearer's skin and stimulate muscles below the skin via electrical impulses. They may also be subcutaneous electrodes, for example electrodes that lie on the nerve.

It has been known from the prior art for many years to control the controllable actuator depending on the detected movement status. To this end, the at least one sensor is configured to record measurement values from which at least one parameter can be determined, the chronological profile of which allows for conclusions to be drawn about a movement status. In this case, the chronological profile need not be detected or evaluated and documented across an entire step cycle. For example, the parameter may be the knee angle of a knee orthosis that is measured, for instance, across a step cycle and evaluated in the electric control system. The maximum knee angle differs depending on the movement status. The maximum angle of flexion that occurs, for example, with a knee is considerably greater when the wearer of the orthopedic device climbs stairs than when they walk on level ground. A conclusion about the movement status can be drawn from this, this information then being used to control the controllable actuator, for example, during the swing phase of the leg in such a way that the arm performs the desired movement.

The limb that is fitted and treated with the orthopedic device is referred to as an ipsilateral limb. Conversely, a limb that is not equipped with the orthopedic device is referred to as a contralateral limb. The contralateral limb may correspond to the ipsilateral limb if both limbs are arms, for example. However, a leg that is not treated with the orthopedic device is also referred to as contralateral if the ipsilateral limb is an arm and vice-versa. Within the meaning of the present invention, this preferably also applies if both are on the same side of the body, i.e. a left arm and a left leg, or a right arm and a right leg.

Measurement values are usually recorded via the at least one sensor, from which parameters of the ipsilateral limb can be determined. For example, the knee angle, the ankle angle, various moments, relative positions of various components to each other, or speeds, accelerations or displacements of certain points of the orthopedic device relative to each other or in absolute terms can be determined. All of these parameters can be used to detect the movement status. However, it is a disadvantage that the movement status can only be detected once the measurement values have been captured, i.e. after or during the respective step. The determination of the movement status can therefore only be done retroactively. In this case, a control of the controllable actuator depending on the detected movement status is always based on the condition that the movement status of the wearer does not change between the two steps. The detected movement status in a step cycle is also deemed applicable for the next step cycle. Disadvantages arise if this is not the case and the movement status changes. If the wearer of the orthopedic device has, for example, a fully or partially paralyzed arm, it may not be able to participate in the swing movement. This has the effect of causing unequal distributions in moments and accelerations and, if necessary, an imbalance. These are offset by the body of the wearer, which may cause malpositions and damages, tensions and/or pain, especially in the hip region, shoulder region and/or the spinal column region. As such, the intended illusion of natural movement is also difficult or impossible to maintain.

The present invention therefore aims to further develop a method for operating an orthopedic device in such a way that the detection of the movement status is improved and the movement performed by the wearer of the orthopedic device with the orthopedic device resembles natural movement as closely as possible.

SUMMARY

The invention solves the problem by way of a method for operating an orthopedic device according to the preamble of claim 1, which is characterized in that at least also the chronological profile of at least one parameter of a second body part of the wearer is used to detect the movement status, wherein the at least one controllable actuator comprises at least one electrode for electro-stimulation that is controlled in such a way that at least one arm of the wearer is caused to swing depending on the detected movement status.

The at least one controllable actuator preferably has at least one electrode for electro-stimulation that is controlled in such a way that an arm of the wearer is caused to swing depending on the detected movement status. However, this is not only of particular interest to wearers who exhibit a paralysis of the treated arm, which is the ipsilateral limb.

In the case of the gait of healthy person, it is not only the two legs that move in coordinated manner. At the same time, the two arms also swing forwards and backwards. The arms swing at an offset to each other, so that one arm swings forwards when the other arm swing backwards.

The specified disadvantages can be prevented by controlling the at least one electrode for electro-stimulation, which forms the controllable actuator, in such a way that the treated arm swings when a corresponding movement status, such as walking, is detected. Preferably, the posterior deltoid is stimulated for backwards swinging and the anterior deltoid for forwards swinging.

Of course, active orthoses can also be controlled correspondingly and thus contribute to a physiological gait and a natural gait pattern.

According to the invention, the chronological profile of a parameter is used to detect the movement status. An individual measurement that provides a measurement value at a single point in time is not enough. It is beneficial, but not necessary, for the chronological profile of the parameter to be determined across one or especially preferably multiple cycles, such as step cycles, particularly in the case of repetitive movements. This is usually done by taking a plurality, preferably a large number, of individual measurements, each of which provides the measurement value at a single point in time. The results of the individual measurements are stored and evaluated as a chronological profile. The plurality of individual measurements may be taken equidistantly in terms of time. The interval between two individual measurements must be small compared to the length of, for example, a step cycle, so that a chronological profile of the parameter can be detected from the plurality of individual measurements.

It is often advantageous and sufficient to determine the chronological profile of the parameter not across entire step cycles, but, for example, only across certain sections of a step cycle. To detect a movement status, it is often enough to know the parameter at very specific points in time of a step cycle, for example. These specific points in time may be, for example, when the heel hits the ground or when the toes come off. To calculate this point in time as precisely as possible, it is necessary or at least advantageous to measure and determine the chronological profile of the parameter in a particular time period before and after this specific point in time. This also falls under the definition of a chronological profile according to the invention.

If the wearer's movement status, i.e. particularly the type of movement, is detected, the controllable actuator can be controlled correspondingly. Preferably, it is not simple routines and chronological profiles stored in a data memory of an electronic control unit for certain movement statuses that are executed. Rather, the chronological profile of the parameter of the second body part is preferably used to control the at least one controllable actuator. As a result, the body part that is supported or replaced by the orthopedic device is moved harmoniously, naturally and in a manner that is adapted to the movements of the other body parts, especially the second body part, as optimally as possible. For example, a natural gait pattern is created by, for example, adapting the movement of an orthopedic device to the movement of a healthy leg, which in this case constitutes the second body part. Alternatively and additionally, the second body part may also be an arm whose natural swinging motion during walking or running is used to control the movement of an arm orthosis.

With the method according to the invention, in particularly advantageous embodiments it is therefore possible to not only detect the wearer's movement status as early as possible and control the at least one controllable actuator accordingly, but also to adapt the movement of the actuator to the movement of various body parts, thereby increasing the wearer's acceptance of the orthopedic device.

In a preferred embodiment, the at least one parameter is a relative position, relative movement and/or relative speed and/or relative acceleration and/or relative angle of the second body part to the first body part and/or of a first part of the second body part to a second part of the second body part. The second body part is preferably a foot, knee, upper leg, lower leg and/or a tendon in the leg. The second body part is preferably an untreated limb or a part thereof. However, it may also be beneficial for the second body part to be, for example, part of a limb on which the orthopedic device is arranged.

To determine the chronological profile of the relative movement, the position of the body parts in relation to each other and/or their position in an overall coordination system relative to at least one sensor are detected at multiple points in time, for example. Position is understood in particular to also mean the translational and/or rotational orientation in relation to each other.

Here, it is irrelevant whether the second body part, particularly the contralateral limb, is treated with another orthopedic device.

Of particular interest is the use of the tendon of an untreated leg as a second body part, said tendon representing the imaginary connecting line between a foot and a hip of the limb. The orientation and length of the leg tendon are particularly interesting measurement values, as well as its speeds and changes. On the one hand, the leg tendon provides information on the position of the foot of the contralateral limb in relation to the center of the body and the center of gravity. It therefore provides direct and indirect information on the progression and stability and/or foot positioning of the wearer. In addition, the movement of the leg tendon can be detected with conventional sensors, even if it not usually used. The movement of the proximal endpoint of the leg tendon, i.e. the hip, can already be calculated via existing sensors, which can be integrated into an orthopedic device described here. Good assumptions can be made about the movement of the distal endpoint, i.e. the foot of the untreated limb, especially in the stance phase. During the swing phase, the movement, i.e. in particular the position and/or change in position, of the foot can be determined via the at least one sensor.

If the proximal endpoint and distal endpoint of the tendon of the untreated leg are known, it is possible, with the aid of, for example, known dimensions of the upper leg and lower leg of the wearer of the orthopedic device, to also determine a leg angle or knee angle that can be intuitively interpreted and used in control principles. The knee angle of the treated side is a proven control parameter.

The relative positions of other points relative to each other, for example the ipsilateral knee axis to the contralateral foot, may also be of interest. The more sensors that are used, the more different parameters there are that are accessible for a measurement. Conclusions can also be drawn about other relative positions via kinematic chains, so that further parameters become accessible.

Conclusions can also be drawn about the segment angle of the contralateral side particularly from the relative positions and/or relative movements as well as the relative angles in various combinations. This affects, for example, the upper leg, the lower leg or the foot. From this, joint angles, such as the contralateral hip angle, knee angle or ankle angle can be determined.

By carefully selecting different sensors for determining different values, from which the various parameters, including those of the second body part, can be determined, conclusions can be drawn, for example, about the contralateral leg movement.

Preferably, the at least one sensor is configured to detect an absolute angle, a relative angle, a speed, an acceleration, a force, a pressure, a pressure wave, a moment, an electrical field and/or a magnetic field. A pressure wave is understood particularly to also mean a sonic wave, especially an ultrasonic wave.

It has been proven advantageous for data of the orthopedic device and/or the wearer to be used for determining the at least one parameter, especially for determining the at least one parameter of the second body part, preferably the contralateral limb. Said data may be, for example, distances, possible swivel angles or length values. For example, to determine a knee angle of a contralateral leg from the leg tendon it is necessary to know, at least roughly, but preferably precisely, the lower leg length and upper leg length of the wearer of the orthopedic device on the contralateral side. Relative values of the contralateral side in relation to the ipsilateral side can also be converted into absolute values by measuring absolute measurement values on the ipsilateral side.

During operation of the orthopedic device, one control variable of the at least one controllable actuator is preferably controlled to a set point or a set point profile. Advantageously, this not only depends on the detected movement status itself, but also on the parameters upon which this detection is based, particularly the at least one parameter of the second body part, preferably the contralateral limb.

The invention also solves the problem by way of an orthopedic device that supports or replaces a first body part, the orthopedic device having at least one sensor and an electric control unit that is configured to carry out a method described here.

When determining the at least one parameter of the contralateral limb, it is possible, as previously explained, to refer back to calculations of the corresponding parameter from sensor data. Alternatively or additionally, missing parameters that are not directly accessible with the used sensors can be determined from existing measurement values and, if applicable, a model or model assumptions. The existing measurement values can be measurement values of both the ipsilateral and contralateral side. Appropriate models are, for example, mechanical and kinematic models that describe the respective movements of the limb.

In an embodiment example, the swing movement of a leg is detected. Some aids do not have any force sensors to determine whether the treated side is in contact with the ground. The contralateral leg movement can provide information on whether it is a backwards walking movement, during which the contralateral stance leg rolls backwards, so that the stimulation of the treated arm can be adapted accordingly.

The invention addresses the stimulation of the upper limb—in particular, but not restricted to, the deltoid—to support the gait pattern. The stimulation amplitude, the chronological profile of the stimulation amplitude and/or the position of the stimulation depending on the sensor values or their chronological profile are determined, wherein these sensor values depend on the current gait phase. Inertial measurement units (IMU) are especially well-suited as sensors. By way of the positioning on the upper or lower leg, the relative position of the limb to the ground can be determined, for example. The use at least two IMUs also enables the relative position of two limbs to each other to be determined (e.g. knee angle, ankle angle). In some circumstances, a prior calibration of the sensors may be necessary to do so.

The sensor values of the acceleration sensors and/or gyroscopes installed in IMUs can also be used to determine, for example, the instantaneous speed or angular speeds and to define the stimulation parameters as a function thereof (e.g. amplitude, position, pulse form).

Using IMUs, the time at which the heel hits the ground can also be determined. To determine the heel strike, the use of a so-called heel switch has been proven effective, especially in combination with drop foot stimulators. Patient-specific stimulation profiles can be triggered in depending, in terms of time, on the heel strike.

The sensor information is processed in a computer (e.g. PC, laptop, microcontroller, . . . ) and converted into corresponding control signals for the stimulator. Ideally, this computer should be connected to the sensors in a portable and wireless manner (e.g. via Bluetooth).

Alternatively, the computer could be integrated directly in the stimulator.

In order to flexibly determine the stimulation points, several stimulation electrodes can be attached to the shoulder and arm. To be able to ensure a simple mounting process, the electrodes can be fixed to orthoses by means of velcro.

However, so-called electrode arrays are preferably used, which enable a positioning of so-called "virtual electrodes" between the physical electrodes of the array via multiplexers and therefore a smooth displacement of stimulation points.

The invention counteracts subluxation and spasticity through stimulation. Particularly during walking, the invention enables a physiological swinging of the arm even with at least one limp arm, which improves the gait pattern and counteracts consequential damage.

Depending on the sensors actually used and the information they provide about the current movement status, the invention can also have a supportive effect in other situations. For example, when turning, standing still or similar situations, the targeted introduction and/or non-introduction of stimulation, among other things, can contribute to improved balance.

BRIEF DESCRIPTION OF THE DRAWINGS

In the following, some examples of embodiments will be explained in more detail by way of the attached figures: They show.

DETAILED DESCRIPTION

Figure 1:
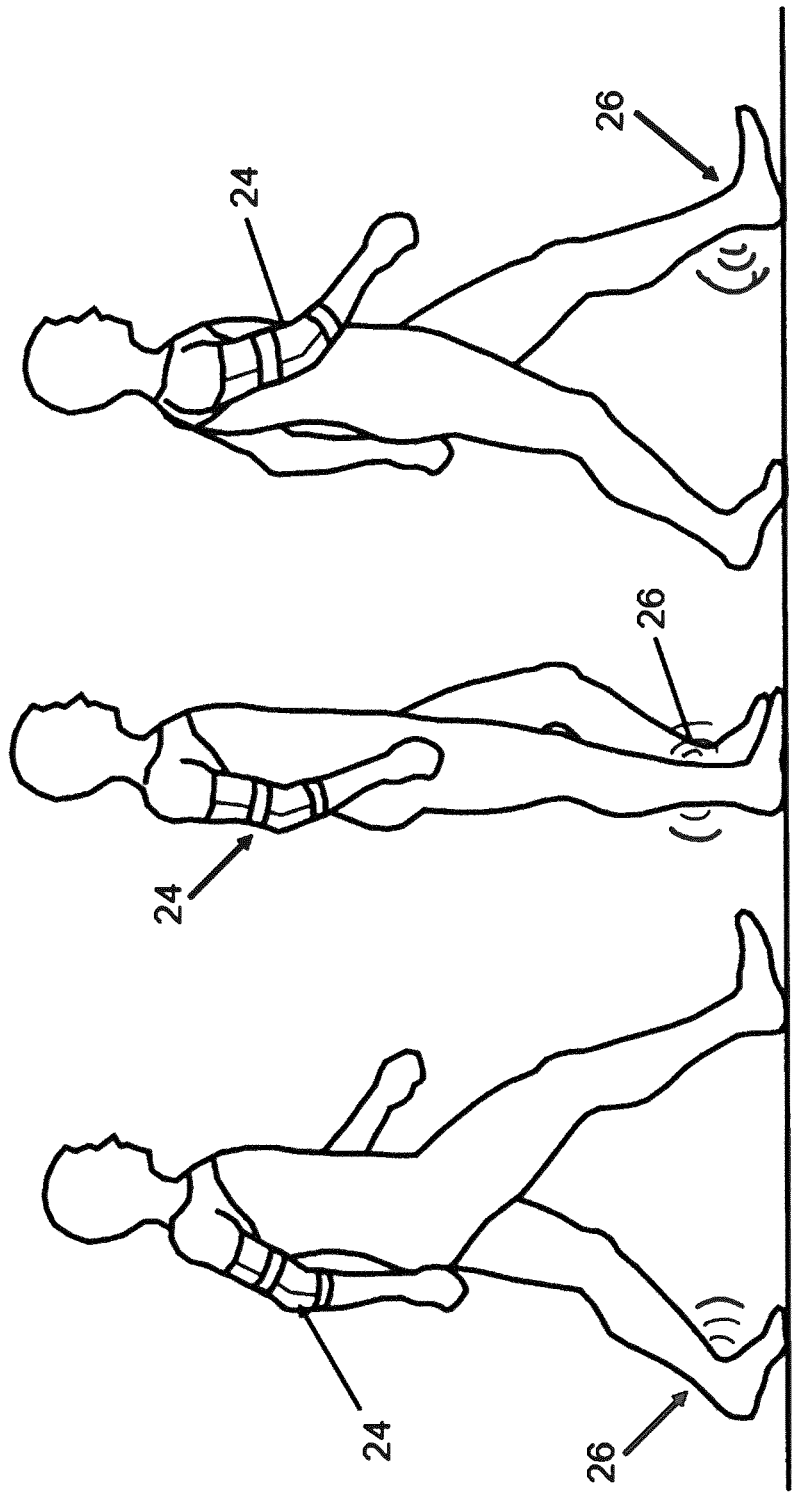
FIG. 1—a schematic representation of an application of a method described here, FIG. 2—a further example of an application, and FIG. 3—a flow diagram.

FIG. 1 is an example of the first body part 24, which is the right arm in the example of an embodiment shown, not necessarily having to lie "opposite" the second body part 26, which is the left ankle in the example of an embodiment shown. FIG. 1 shows three positions within a step cycle where in each case the position of the second body part 26, i.e. the left ankle, relative to a further body part, namely the right ankle, is determined. In the left-hand representation in FIG. 1 the second body part 26 is behind the wearer's torso. The same applies for the first body part 24. The relative position of the second body part 26 relative to the right ankle is determined, which is indicated by the three short lines. In the course of the step cycle, the position of the second body part 26 relative to the right ankle changes via the positions shown in the middle of FIG. 1 during the swing phase until it reaches the position shown on the right in FIG. 1 when the heel strikes the ground. Correspondingly, the movement of the first body part 24, which is replaced by an arm orthosis, is also controlled.

Figure 2:
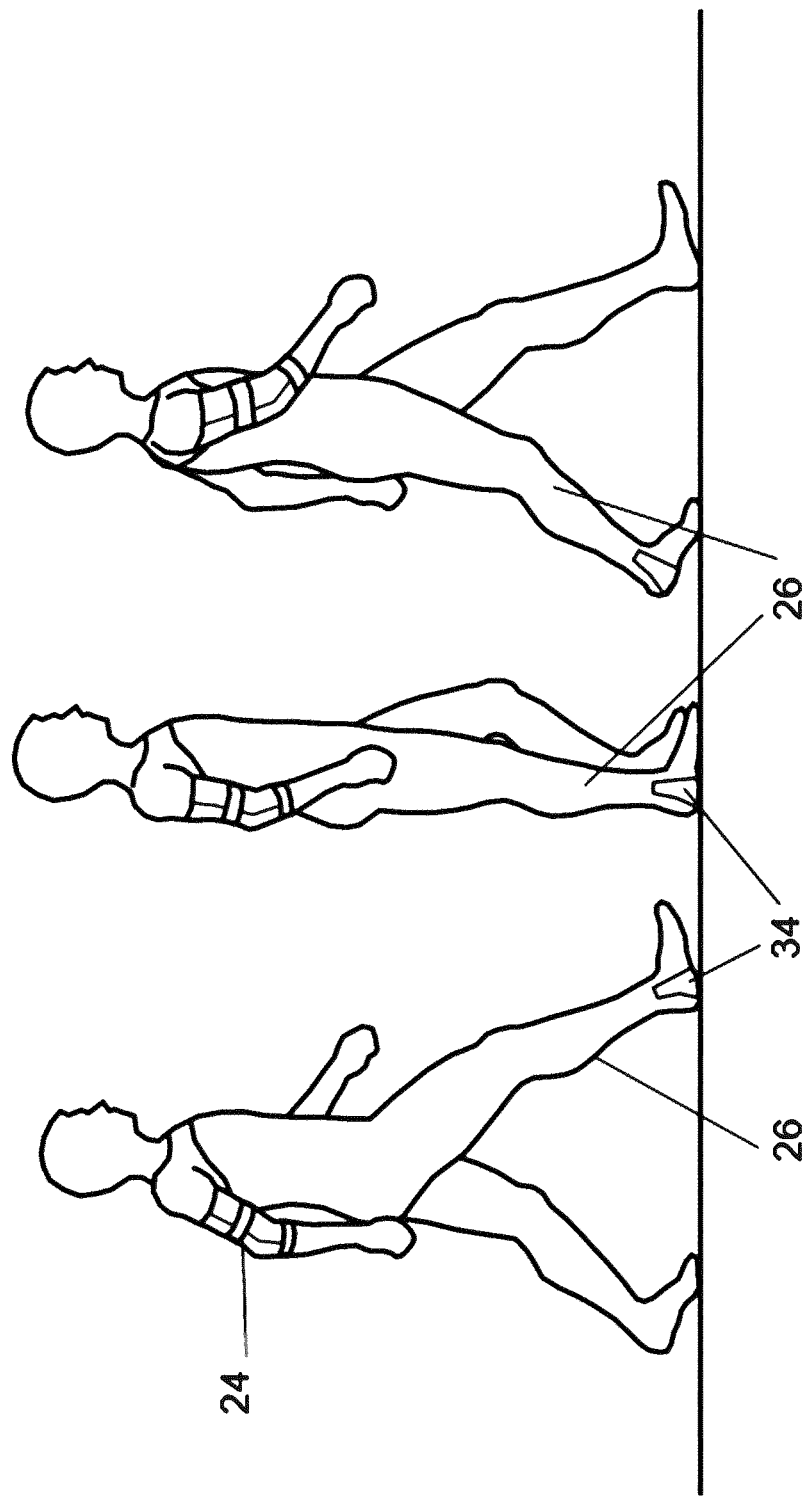

FIG. 2 is an example of the second body part 26, on which a sensor 34 is mounted for determining the movement status, particularly the stance phase in the step cycle, being able to be located on the same half of the body as the body part 24, which is fitted with an orthopedic aid. This sensor can—as in the case of a heel switch, for example—obtain information about the movement status solely on the basis of measurements of the limb 26 equipped with the sensor 34. The sensor 34 mounted on the body part 26 can also be used to receive measuring beams that are emitted by the opposite leg or reflected or re-emitted.

Figure 3:
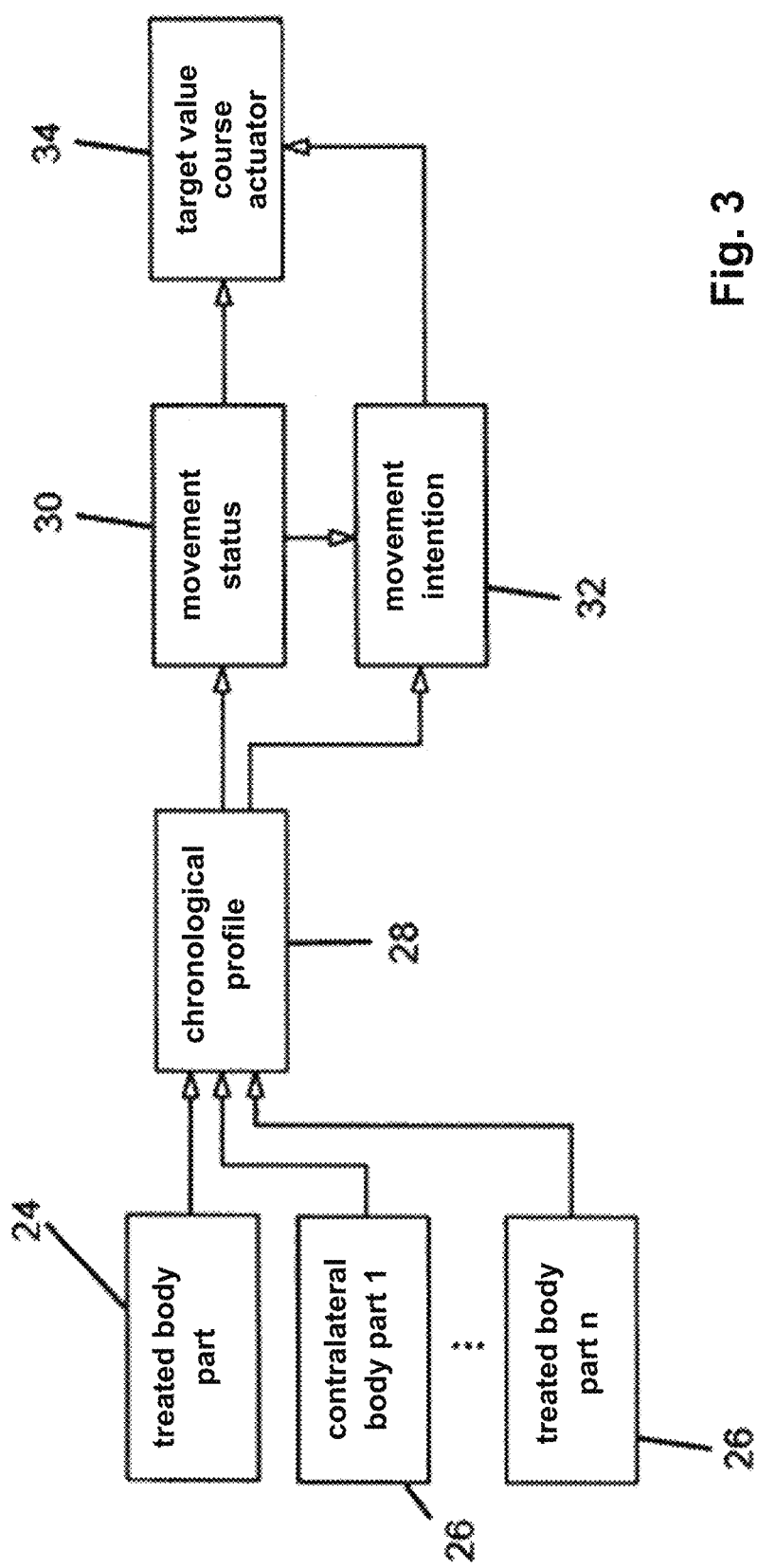

FIG. 3 depicts a schematic flow diagram for a method described here. Parameters are calculated from a first body part 24 and at least a second body part 26; the chronological profile of said parameters is then determined. Both a movement status 30 and movement intention 32 of the wearer are determined from this profile, wherein the determined movement status 30 can also be consulted to determine the movement intention 32. Both the movement intention 32 and the determined movement status 30 can be used separately from each other or in combination to initiate the actuator control unit 34.

REFERENCE LIST 2 contralateral limb
4 ipsilateral limb
6 upper leg socket
8 knee joint
10 lower leg
12 foot
14 measuring radiation
16 lower leg socket
18 upper leg frame
20 lower leg frame
22 knee joint
24 first body part
26 second body part
28 chronological profile
30 movement status
32 movement intention
34 sensor

The invention claimed is:

1. A method for operating an orthopedic device which supports a first body part of a wearer, and
comprises at least one controllable actuator,
wherein the method comprises the following step:
  a) determining at least one chronological profile of at least one parameter, which allows for a conclusion to be drawn about a movement status of the wearer, from measurement values of at least one sensor,
  b) detecting the movement status of the wearer from the at least one determined chronological profile, and
  c) controlling the at least one controllable actuator depending on the detected movement status of the wearer, wherein
  at least also the chronological profile of at least one parameter of a second body part of the wearer is used to detect the movement status of the wearer, wherein the at least one controllable actuator comprises at least one electrode for electro-stimulation that is controlled in such a way that at least one arm of the wearer is caused to swing depending on the detected movement status of the wearer.

2. The method according to claim 1, wherein the at least one parameter is a relative position, relative movement, relative speed, relative acceleration and/or relative angle of the second body part to the first body part and/or of a first part of the second body part to a second part of the second body part.

3. The method according to claim 1, wherein the at least one sensor is configured to detect an absolute angle, a relative angle, a speed, an acceleration, a force, a pressure, a pressure wave, a moment, an electrical field and/or a magnetic field.

4. The method according to claim 1, wherein data of the orthopedic device and/or the wearer is used to determine the at least one parameter of the second body part.

5. An orthopedic device for supporting a first body part of a wearer, the orthopedic device comprising:
at least one controllable actuator, at least one sensor and one electric control unit configured to:
determine a chronological profile of at least one parameter, which allows for a conclusion to be drawn about a movement status of the wearer from measurement values from the at least one sensor;
detect the movement status of the wearer from the at least one determined chronological profile; and
control the at least one controllable actuator depending on the detected movement status of the wearer; wherein
at least the chronological profile of the at least one parameter of a second body part of the wearer is used to detect the movement status; wherein the at least one controllable actuator comprises at least one electrode for electro-stimulation that is controlled in such a way that at least one arm of the wearer is caused to swing depending on the detected movement status of the wearer.

6. The orthopedic device of claim 5, wherein the at least one parameter is a relative position, relative movement, relative speed, relative acceleration and/or relative angle of the second body part to the first body part and/or of a first part of the second body part to a second part of the second body part.

7. The orthopedic device of claim 5, wherein the at least one sensor is configured to detect an absolute angle, a relative angle, a speed, an acceleration, a force, a pressure, a pressure wave, a moment, an electrical field and/or a magnetic field.

8. The orthopedic device of claim 5, wherein data from the orthopedic device and/or the wearer is used to determine the at least one parameter of the second body part.

9. A method for operating an orthopedic device which supports a first body part of a wearer, and comprises at least one controllable actuator, wherein the method comprises:
a) determining at least one chronological profile of at least one parameter from measurement values of at least one sensor, allowing for a conclusion to be drawn about a movement status of the wearer;
b) detecting the movement status of the wearer from the at least one determined chronological profile; and
c) controlling the at least one controllable actuator depending on the detected movement status of the wearer;
wherein a chronological profile of at least one parameter of a second body part of the wearer is used to detect the movement status of the wearer;
wherein data from the orthopedic device and/or the wearer is used to determine the at least one parameter of the second body part; and
wherein the at least one controllable actuator comprises at least one electrode for electro- stimulation that is controlled in such a way that at least one arm of the wearer is caused to swing depending on the detected movement status of the wearer.

10. The method according to claim 1, wherein the at least one parameter is a relative position, relative movement, relative speed, relative acceleration and/or relative angle of the second body part to the first body part and/or of a first part of the second body part to a second part of the second body part.

11. The method according to claim 1, wherein the at least one sensor is configured to detect an absolute angle, a relative angle, a speed, an acceleration, a force, a pressure, a pressure wave, a moment, an electrical field and/or a magnetic field.

* * * * *